United States Patent [19]

Legille

[11] 4,061,036
[45] Dec. 6, 1977

[54] DEVICE FOR THE EXTRACTION OF GASEOUS SAMPLES AND FOR THERMAL MEASUREMENT ABOVE THE BURDEN OF A SHAFT FURNACE

[75] Inventor: Edouard Legille, Luxembourg, Luxembourg

[73] Assignee: S.A. des Anciens Etablissements Paul Wurth, Luxembourg

[21] Appl. No.: 706,947

[22] Filed: July 20, 1976

[30] Foreign Application Priority Data

July 24, 1975 Luxembourg .......................... 73050

[51] Int. Cl.² .............................................. G01N 1/22
[52] U.S. Cl. ............................................. 73/421.5 A
[58] Field of Search ..................... 73/421.5 R, 421.5 A

[56] References Cited

U.S. PATENT DOCUMENTS 3,885,437  5/1975  Reagan ........................... 73/421.5 A
3,888,123  6/1975  Kuntziger ....................... 73/421.5 A

FOREIGN PATENT DOCUMENTS 914,700  2/1963  United Kingdom ........... 73/421.5 A

Primary Examiner—S. Clement Swisher
Attorney, Agent, or Firm—Holman & Stern

[57] ABSTRACT

A device for the extraction of gaseous samples and for thermal measurement above the burden of a shaft furnace includes at least one probe arm resonantly positioned in a horizontal plane above the burden. Means are provided for pivoting the probe arm above the burden from a rest position juxtaposed the furnace wall so that the entire surface of the burden can be scanned.

10 Claims, 4 Drawing Figures

DEVICE FOR THE EXTRACTION OF GASEOUS SAMPLES AND FOR THERMAL MEASUREMENT ABOVE THE BURDEN OF A SHAFT FURNACE

BACKGROUND OF THE INVENTION

The present invention relates to a device for the extraction of gaseous samples and for thermal measurement above the burden of a shaft furnace, particularly a blast furnace.

It is known that one of the essential conditions for the optimum operation of a shaft furnace is that the gases should traverse the furnace in a faultless manner and that the ascending currents of gas should be uniformly distributed over the entire cross section of the furnace. After each charging operation, however, disturbances take place in the gaseous currents and may prevent the gases from traversing the furnace evenly. In order to remedy this drawback and to decide on the measures required, such as a change in the distributing of the charge, the composition of the gases and the temperature prevailing above the burden must be constantly monitored in order to detect any irregularity or sudden change in the operation of the furnace.

The known devices for the extraction of samples of gas and for thermal measurements above the burden of a shaft furnace comprise one or more probes, positioned radially above the burden and provided with gas sample extraction orifices. These known probes are either fixed, in which case the material of the burden is liable to fall on them while the furnace is being charged, or radially movable into and out of the furnace, in which case they have to be mounted in a special manner, causing a certain amount of obstruction, around the periphery of the furnace, in order to support them on the outside thereof.

The fixed probes and the radially movable probes no longer satisfy the requirements of modern blast furnaces having charging installations without bells (cones), such as that proposed, for example, in Luxembourg Pat. No. 59,207. These charging installations comprise a rotary spout which serves to discharge the material and of which the angle in relation to the vertical axis is adjustable, so that they enable the material to be distributed above the burden in the manner desired. To enable optimum use to be made of this spout and to take advantage of all the possibilities which it offers, the probe or probes positioned above the burden should be capable of providing measuring results for all points on the surface of the burden, so that the spout, which itself is capable of serving any point on the surface, can be controlled in accordance with these readings. The known probes give very little indication of the composition and the temperature over the entire cross section of the furnace and therefore do not provide a means for the detection of a local irregularity. The reason is that the probes are positioned radially without being capable of performing any angular movement about the vertical axis of the furnace. The measuring readings thus simply represent the gas composition and the temperature along one or more radii, according to the number of probes, above the burden.

SUMMARY OF THE INVENTION

The object of the present invention is to provide a device for the extraction of gaseous samples and for thermal measurement which will supply readings over the entire surface of the burden, particularly for the purpose of obtaining measurements usable for automatic control of the charging process.

To achieve its object the present invention provides for a device for the extraction of gaseous samples and for thermal measurement above the burden of a shaft furnace, particularly a blast furnace, comprising at least one probe arm situated in a substantially horizontal plane above the burden, and means for moving each probe arm above the burden in such a way as to scan practically the entire surface of the burden.

One preferred embodiment of the invention comprises three probe arms pivotable about three different vertical axes respectively, the axes being situated around the periphery of the furnace at 120° intervals.

BRIEF DESCRIPTION OF THE DRAWINGS

Further advantages and characteristics will become apparent from the detailed description of two versions of the invention, discussed as illustrations thereof and by reference to the accompanying schematic drawings, in which.

DETAILED DESCRIPTION OF THE PREFERRED EMBODIMENTS

Figure 1:
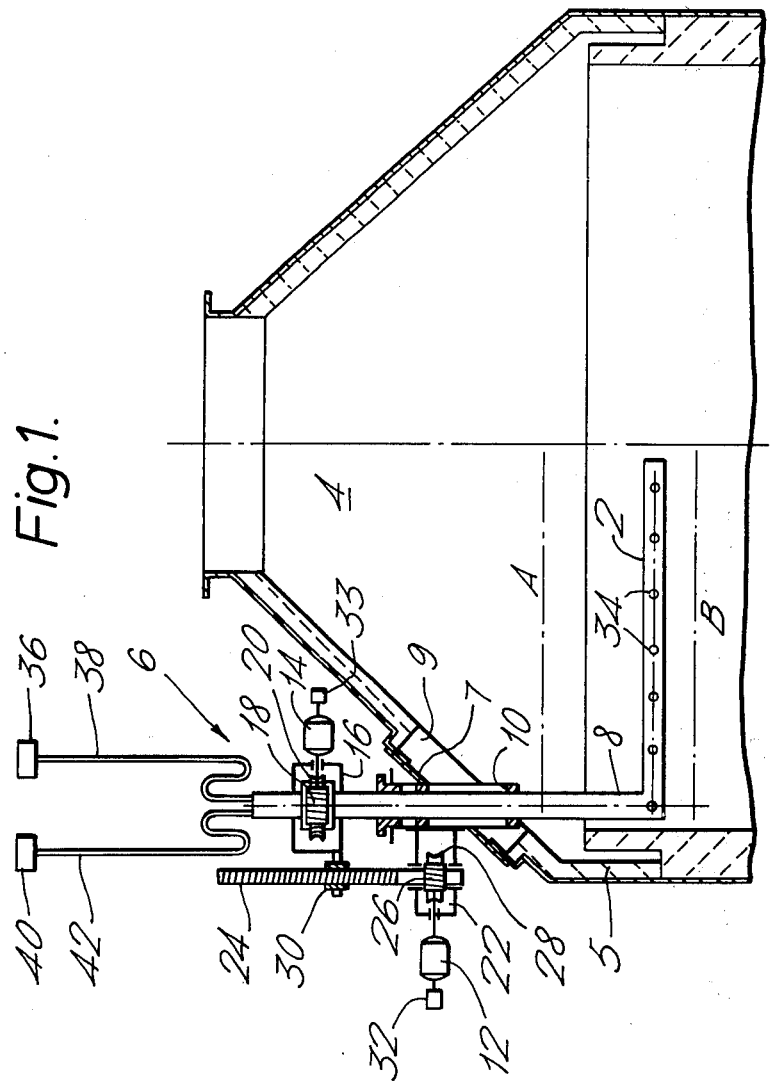
FIG. 1 is a vertical section through the throat of a blast furnace, with a control mechanism and with a probe arm according to a first version of the invention.

FIG. 1 shows a probe arm 2 situated in a substantially horizontal plane above the burden of a blast furnace 4 and displaceable vertically and horizontally by means of a control mechanism 6 situated outside the blast furnace 4. In the peripheral region of the blast furnace the probe arm 2 is connected to the control mechanism 6 via a vertical pipe 8 passing through a packing 10 in the upper wall 5 of the blast furnace 4. The packing 10 enables the pipe 8 to rotate and slide vertically while at the same time ensuring adequate hermeticity.

The control mechanism 6 comprises two separate drives, one for the horizontal pivoting movement and the other for the vertical displacement of the probe arm 2. FIG. 1 shows two motors 12 and 14 designed to control the vertical movement and the horizontal pivoting movement, respectively, of the probe arm 2. The motor 14 is connected to a first gear case 16 mounted around the vertical pipe 8. The gear case 16 contains a worm gear consisting of a worm 18 affixed to the shaft of the motor 14 and driving a pinion 20 which is integral with the vertical pipe 8, which passes through the gear case 16. By means of the gearing connection between the worm 18 and the pinion 20, therefore, the rotation of the motor 14 causes the pipe 8 to rotate in relation to the gear case 16, resulting in a pivoting movement of the probe arm 2 about the vertical axis of the pipe 8. The motor 12 is connected to a second gear case 22 affixed to the wall of the blast furnace 4 and mounted around a screw-threaded vertical bar 24 parallel with the pipe 8. The gear case 22, like the gear case 16, contains a worm gear consisting of a worm 26 affixed to the shaft of the motor 12 and driving a pinion 28 integral with the screw-threaded bar 24 traversing the gear case 22. A traverse 30, integral with the gear case 16, comprises a screw-threaded bore by which it is connected to and interacts with the threading of the vertical bar 24. By means of the gearing connection between the worm 26 and the pinion 28, therefore, the rotation of the motor 12 causes the threaded bar 24 to rotate in relation to the gear case 22, resulting in a vertical displacement of the traverse 30 on the threading of the bar 24. Now since the traverse 30 is integral with the gear case 16, which in its turn is integral with the pipe 8, in accordance with the axial direction of the latter, a vertical movement of the traverse 30 results in a corresponding displacement of the gear case 16, the motor 14 of the pipe 8 and the horizontal probe arm 2.

The control mechanism 6 thus provides movement of the probe arm 2 either vertically, between an upper limit A and a lower limit B, by actuating the motor 12, or horizontally by a pivoting movement about the axis of the pipe 8, by actuating the motor 14, or both vertically and horizontally by actuating both motors 12 and 14 at the same time, if this proves necessary.

The two motors 12 and 14 are connected to two selsyn positioning devices 32 and 33 respectively, to indicate the momentary position of the probe arm 2.

The invention is obviously not confined to the driving mechanism 6 illustrated by way of example in FIG. 1 and includes any means equivalent to the mechanism 6, i.e. any device capable of causing the pipe 8 to perform an axial and/or angular movement.

The probe arm 2 comprises a series of apertures 34 distributed over the entire length of the probe arm 2 and serving for the extraction of gas samples. The apertures 34 are individually connected, via conduits through the probe arm 2, the pipe 8 and a flexible tube 38, to a distributor 36 which is mounted outside the blast furnace 4 and from which the various samples of gas can be conveyed simultaneously, and through separate conduits, into collecting tanks, or else directly to an analyzer, not shown in the drawings. Each of the apertures 34 contains a thermal pick-up, such as a thermoelectric element, which is swept over by the gas samples of which it measures the temperature. Electrical signals representing the temperature measurements effected in the apertures 34 are likewise transmitted to the distributor 36, which conveys them to an indicator, not shown in the drawings.

In order to complete the indications concerning the characteristics of the gas above the burden in the blast furnace a pressure indicator may be provided, either in the probe arm 2 or in the distributor 36.

In order to avoid deterioration of the probe arm 2 as a result of heating, it is advantageously traversed by a cooling fluid which may consist of a gas or of water. To enable this cooling system to operate, the probe arm is advantageously connected by means of a flexible conduit 42 to a water outlet 40 from a water supply system or from the blast furnace cooling circuit.

The packing 10, which enables the vertical pipe 8 to pass through the interior of the furnace 4 and which at the same time ensures adequate hermeticity in order to avoid any leakage of gas and eliminate the risk of accident, is affixed to a plate 7 which covers an orifice 9 in the upper wall 5 of the furnace 4. The plate 7 is easily removable, so that the pipe 8 and the probe arm 2 can be withdrawn through the orifice 9 if necessary.

The control mechanism and also the sample extraction and measuring means described in detail above, in conjunction with the probe arm 2, are the same for the other probe arms mounted above the furnace burden and not shown in FIG. 1, regardless of the number of arms. The number of arms may vary but is preferably three.

Figure 2:
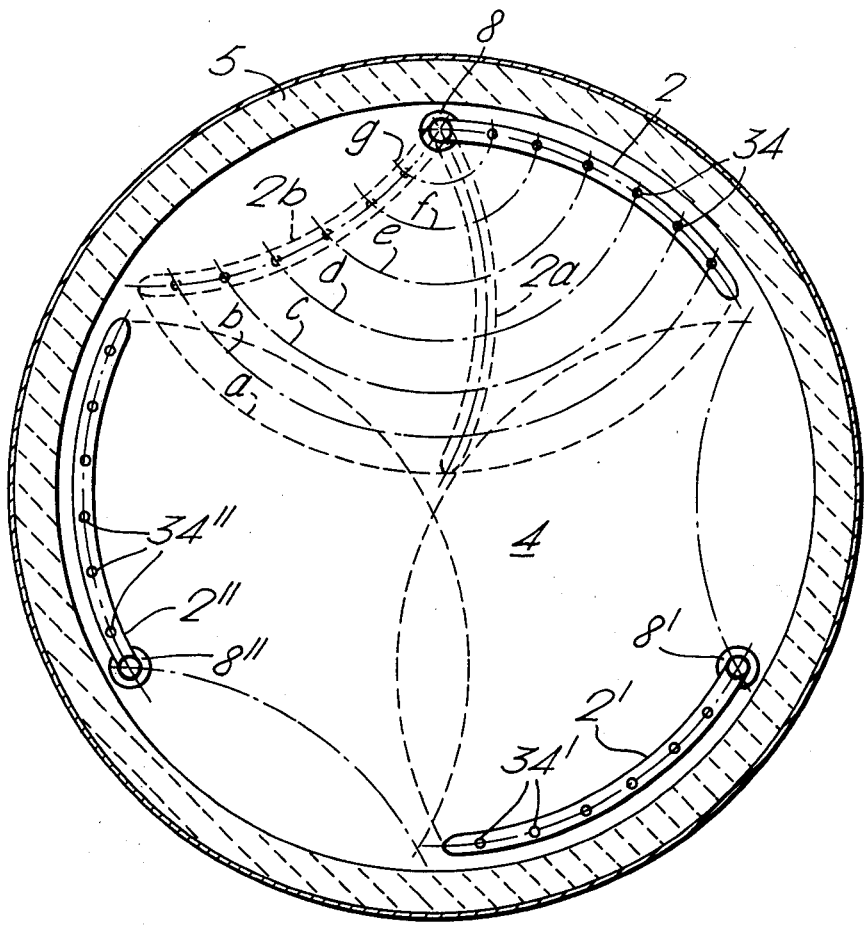
FIG. 2 shows a horizontal section, passing through three probe arms according to FIG. 1.

FIG. 2 is a horizontal section through three probe arms 2, 2' and 2", the arms 2' and 2" being identical to the arm already described in conjunction with FIG. 1. The three probe arms 2, 2' and 2" are curved in the horizontal plane, forming a circular arc of which the curvature fits that of the wall 5 of the blast furnace. The probe arms can thus be turned back to their position of rest (shown in full lines in FIG. 2) against the wall 5 of the blast furnace 4.

When the motors for the horizontal displacement of the probe arms 2, 2' and 2" are actuated, as described with reference to probe arm 2 in FIG. 1, the probe arms will effect a pivoting movement about the vertical axis of the pipes 8, 8' and 8". Each of these probe arms 2, 2' and 2" thus moves through a circular sector of about 120°, about the axes of the pipes 8, 8' and 8". FIG. 2 shows, in dotted lines, an extreme position 2b and an intermediate position 2a of the probe arm 2, the corresponding positions of the probe arms 2' and 2" having been deliberately omitted. As shown in dot-and-dash lines a, b, c, d, e, f and g, each of the apertures 34, as well as the end of the arm 2, describes a circular arc between the position of rest of the probe arm 2 and the extreme position 2b. The same applies to all the apertures 34' and 34" of the probe arms 2' and 2", and the simultaneous pivoting movement of the three probe arms thus enables the entire surface above the burden to be swept.

The number of probe arms is not limited to three, but FIG. 2 shows that this number is sufficient to cover approximately the entire surface of the section. This is why the probe arms are preferably three in number. It should be noted that, in all instances where there are more than one probe arm, the length of the arms must not exceed the radius of the blast furnace, so that the different arms will not catch on one another in the center, on the longitudinal axis of the furnace.

An essential advantage of the sampling device according to the present invention resides in the fact that the probe arms, unlike systems hitherto known, enable the entire surface of the furnace burden to be swept. The measuring results thus provide an overall picture of the entire surface of the burden, whereas the measurements obtained with the conventional probes merely correspond to one or more radial lines. The surface of the burden can be swept by the three probe arms either continuously or step-by-step. The two methods can be applied very easily with one and the same motor 14 by combining the motor with the appropriate control system.

A further advantage offered by the invention in comparison with systems already known resides in the fact that each probe arm can be individually moved in the vertical direction, independently of the horizontal movement. This enables the probe arms to be raised or lowered in accordance with the level to which the furnace is charged, so that they will always be moving just above the burden. To obtain accurate local measurements and determine the passage of gases through the burden with a greater degree of precision it is essential that the samples be extracted and the thermal measurements effected on a level with the burden, in order to avoid collecting gas mixtures emanating from different places, thus falsifying the measurements.

As the probe arms are controlled individually it is possible to operate them at different levels. Although this method of operation is not generally required it nevertheless provides an example of the numerous possibilities offered for the use of the probes covered by the present invention.

As each probe arm can be turned all the way back against the wall 5 of the blast furnace 4 and raised as far as the maximum level A, each probe arm can be moved out of the way of the falling material during the charging process without having to remove each probe arm from the furnace, an object which cannot be achieved in existing systems.

The motor 12 which controls the vertical movement of the probe arm 2 and also the corresponding motors for the probe arms 2' and 2" can be connected into a servo-circuit which comprises, inter alia, a "trailing probe", in accordance with Luxembourg Pat. No. 64,587, to determine the upper level and the profile of the burden. Each probe arm can thus be adjusted vertically, so that the arms will be situated just above the surface of the burden.

A slip coupling, not shown in the drawings, can be interposed between the motor 14 controlling the horizontal sweeping movement and the gear case 16. The coupling would enable the gears of the gear case 16 to be shut off and the movement of the probe arm 2 to be stopped, the motor 14 continuing to operate, when the resistance to horizontal movement of the probe arm increases beyond the normal level. This may be the case, for example, when the probe arm 2 encounters an obstacle or an abnormal irregularity in the profile of the burden during the sweeping process. In this case the other motor 12 will be actuated (which could even be done automatically) in order to raise the probe arm so that the probe arm can continue the sweeping movement, by passing over the obstacle in question.

Figure 3:
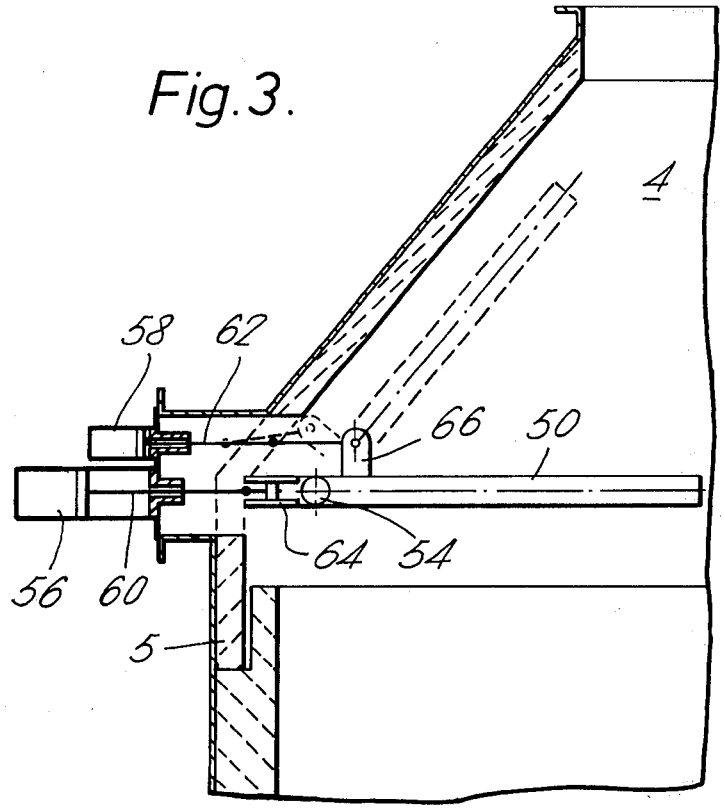
FIGS. 3 and 4 show a vertical section and a horizontal section, respectively, of a probe arm with a control mechanism according to a second version of the invention.
Figure 4:
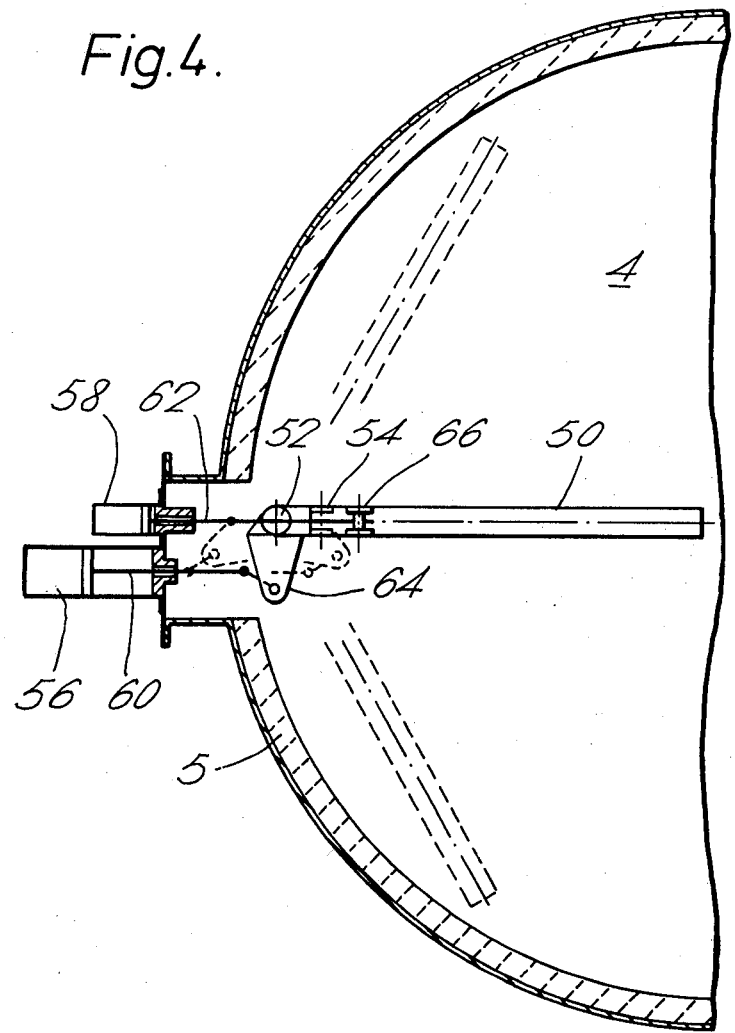

The schematic drawings shown in FIGS. 3 and 4 illustrate a vertical section and a horizontal section respectively of a second version of a gas sampling and thermal measuring device according to the present invention. In these drawings a probe arm 50, represented by full lines, is positioned in a substantially horizontal plane above the burden of a blast furnace 4. The probe arm comprises a joint 52 with a vertical axis and a joint 54 with a horizontal axis. These two joints 52 and 54 respectively enable the probe arm to pivot in a horizontal plane between the two positions indicated by broken lines in FIG. 4 and in a vertical plane between the two positions indicated by full lines and broken lines in FIG. 3.

The movements of the probe arm 50 are performed with the aid of two separate hydraulic jacks 56 and 58 which are affixed horizontally to the outside of the furnace and have bars 60 and 62 which traverse the furnace wall 5. The bar 62 of the jack 58 is connected to a vertical pivot 66 affixed to the probe arm 50 and serves to raise the probe arm to the position shown by broken lines in FIG. 3. This last position is taken by the probe arm 50 when the blast furnace is being charged so that the probe arm is out of the way of the falling material.

The bar 60 of the jack 56 is connected to a horizontal pivot 64 affixed to the probe arm 50 and serves to move the probe arm between the two positions indicated by broken lines in FIG. 4. The jack 56 is thus actuated either continuously or step-by-step, in order to cause the probe arm 50 to perform its horizontal sweeping movement.

The sampling and measuring operations are effected in an identical manner and by similar means to those of the version shown in FIGS. 1 and 2 and will therefore not be fully described with reference to or shown in detail in FIGS. 3 and 4.

Whether the device shown in FIGS. 1 and 2 or that shown in FIGS. 3 and 4 is adopted, the present invention enables measurements to be carried out at approximately all points on the surface of the burden, so that any variations in the chemical composition or in the temperature over the entire section of the blast furnace can be faithfully reproduced. The knowledge thus provided makes it possible, in its turn, to draw conclusions regarding the operation of a furnace and the remedial action to be adopted for any defects.

The results of the analysis of the gas samples and of the temperature may be recorded in graphs by means of a recorder of which the operation is synchronized with the movement performed by the probe arms sweeping over the burden. The readings can thus be used in order to prepare control signals for proportioning and/or distributing the material in any automatic blast furnace charging operation.

Although the maximum advantage can be derived from the possibilities offered by the present inventive device for extracting gas samples and taking thermal measurements above the burden of the shaft furnace is in connection with the known charging device having a variable-angle rotary spout, it is obvious that the application of the inventive device is not to be confined to charging operations of the type mentioned. The device covered by the present invention can be easily adapted to existing blast furnaces, whether with or without bells (cones).

I claim:

1. A device for the extraction of gaseous samples and for thermal measurement above the burden of a shaft furnace, the device comprising at least one probe arm permanently positioned in a substantially horizontal plane above the burden; a series of apertures distributed over the entire length of the probe arm and conduits communicating separately with each of the apertures and with the exterior of the furnace; and means for pivoting the probe arm from a rest position juxtaposed the inside wall of said shaft furnace across and above the burden in such a way as to scan practically the entire surface of the burden, said pivot means having at least one pivot axis juxtaposed the inside wall of said shaft furnace.

2. The device as claimed in claim 1, further comprising a thermoelectric element within each aperture and serving to determine the temperature of the gaseous sample extracted through each aperture.

3. The device as claimed in claim 2 further comprising means including conduits for causing a cooling fluid to circulate in each probe arm.

4. The device as claimed in claim 1, wherein there are three probe arms, capable of pivoting about three vertical axes respectively, the probe arms being offset in relation to one another by 120° around the periphery of the furnace.

5. The device as claimed in claim 1, wherein the means for moving each probe arm comprises a vertical pipe integral with the probe arm and passing through a packing in the upper wall of the furnace and, outside the furnace, a control mechanism connected to the vertical pipe and capable of causing the vertical pipe to perform an axial movement and an angular movement.

6. The device as claimed in claim 5, wherein the control mechanism comprises a first motor, a first gear case traversed by the vertical pipe and connected to the first motor in order to cause the vertical pipe to perform an angular movement, a second motor, a second gear case connected to the second motor and traversed by a screw-threaded bar which interacts with a traverse integral with the first gear case, the rotation of the second motor resulting, via a rotation of the threaded bar, in a vertical movement of first gear case, the first motor, the vertical pipe and the probe arm.

7. The device as claimed in claim 3, wherein the transmission conduits for the gas samples and the thermal measurements, and the cooling fluid conduits pass through the vertical pipe.

8. The device as claimed in claim 5, wherein each probe arm is curved in a horizontal plane, describing a circular arc having a curvature similar to that of the wall of the furnace.

9. The device as claimed in claim 1, wherein each probe arm comprises a joint with a horizontal axis about which the probe arm can pivot in a vertical plane and a joint with a vertical axis about which the probe arm can pivot in a horizontal plane.

10. The device as claimed in claim 9, wherein each probe arm comprises a horizontal pivot and a vertical pivot and further comprising two hydraulic jacks mounted outside the furnace and having bars connected respectively to the horizontal and vertical pivot, for the purpose of pivoting the probe arm in a vertical plane and in a horizontal plane respectively.

* * * * *